United States Patent
Dagher et al.

(10) Patent No.: US 10,067,211 B2
(45) Date of Patent: Sep. 4, 2018

(54) SYSTEM AND METHOD FOR ESTIMATING PHASE MEASUREMENTS IN MAGNETIC RESONANCE IMAGING

(71) Applicants: Joseph Dagher, Tucson, AZ (US); Audrey Fan, Cambridge, MA (US); Ali Bilgin, Tucson, AZ (US)

(72) Inventors: Joseph Dagher, Tucson, AZ (US); Audrey Fan, Cambridge, MA (US); Ali Bilgin, Tucson, AZ (US)

(73) Assignees: The General Hospital Corporation, Boston, MA (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 577 days.

(21) Appl. No.: 14/650,647

(22) PCT Filed: Dec. 10, 2013

(86) PCT No.: PCT/US2013/074085
§ 371 (c)(1),
(2) Date: Jun. 9, 2015

(87) PCT Pub. No.: WO2014/093320
PCT Pub. Date: Jun. 19, 2014

(65) Prior Publication Data
US 2015/0369896 A1   Dec. 24, 2015

Related U.S. Application Data (60) Provisional application No. 61/856,394, filed on Jul. 19, 2013, provisional application No. 61/735,278, filed on Dec. 10, 2012.

(51) Int. Cl.
*G01V 3/00* (2006.01)
*G01R 33/50* (2006.01)
(Continued)

(52) U.S. Cl.
CPC .......... *G01R 33/5608* (2013.01); *A61B 5/055* (2013.01); *G01R 33/34* (2013.01);
(Continued)

(58) Field of Classification Search
CPC ...... G01R 33/34; G01R 33/56; G01R 33/385; G01R 33/4808; G01R 33/5608; G01R 33/5615
See application file for complete search history.

(56) References Cited

U.S. PATENT DOCUMENTS

| 4,720,679 A | 1/1988 | Patrick et al. |
| 5,218,299 A | 6/1993 | Dunkel |

(Continued)

FOREIGN PATENT DOCUMENTS

| WO | 2004/102173 A2 | 11/2004 |
| WO | 2012/129585 A1 | 10/2012 |

OTHER PUBLICATIONS

The International Search Report and Written Opinion as dated Apr. 10, 2014 for International Application PCT/US2013/074085.
(Continued)

*Primary Examiner* — Minh N Tang
(74) *Attorney, Agent, or Firm* — Quarles & Brady LLP (57) ABSTRACT

Described here are systems and methods for estimating phase measurements obtained using a magnetic resonance imaging (MRI) system such that phase ambiguities in the measurements are significantly mitigated. Echo time spacings are determined by optimizing phase ambiguity functions associated with the echo time spacings. Data is then acquired using a multi-echo pulse sequence that utilizes the determined echo spacings. Phase measurements are then estimated and images are reconstructed using a reconstruction technique that disambiguates the phase ambiguities in the phase measurements.

14 Claims, 3 Drawing Sheets (51) Int. Cl.
   *G01R 33/56*    (2006.01)
   *A61B 5/055*    (2006.01)
   *G01R 33/561*   (2006.01)
   *G01R 33/565*   (2006.01)
   *G01R 33/34*    (2006.01)
   *G01R 33/385*   (2006.01)
   *G01R 33/48*    (2006.01)
   *A61B 5/00*     (2006.01)

(52) U.S. Cl.
   CPC ....... *G01R 33/385* (2013.01); *G01R 33/4806* (2013.01); *G01R 33/56* (2013.01); *G01R 33/5615* (2013.01); *G01R 33/56554* (2013.01); *A61B 5/7285* (2013.01); *G01R 33/5616* (2013.01)

(56) References Cited

U.S. PATENT DOCUMENTS

2010/0283463 A1* 11/2010 Lu ................... G01R 33/243
                                                    324/309
2014/0375318 A1* 12/2014 Dagher ............. G01R 33/243
                                                    324/309

OTHER PUBLICATIONS

Rodriguez, Pedro A. et al., Phase Ambiguity Correction and Visualization Techniques for Complex-Valued ICA of Group fMRI Data, Pattern Reconit, Jun. 1, 2012; 45(6): 2050-2063, abstract, introduction.

* cited by examiner

SYSTEM AND METHOD FOR ESTIMATING PHASE MEASUREMENTS IN MAGNETIC RESONANCE IMAGING

CROSS-REFERENCE TO RELATED APPLICATIONS

This application represents the U.S. National Stage of International Application No. PCT/US2013/074085, filed Dec. 10, 2013 which is based on, claims the benefit of, and incorporates herein by reference U.S. Provisional Patent Application Ser. No. 61/735,278, filed Dec. 10, 2012, and titled, "SYSTEMS AND METHODS FOR FIELD MAP ESTIMATION," and U.S. Provisional Patent Application Ser. No. 61/856,934, filed Jul. 19, 2013, and titled, "SYSTEM AND METHOD FOR ESTIMATING PHASE MEASUREMENTS IN MAGNETIC RESONANCE IMAGING."

STATEMENT REGARDING FEDERALLY SPONSORED RESEARCH

N/A

BACKGROUND OF THE INVENTION

The field of the invention is systems and methods for magnetic resonance imaging ("MRI"). More particularly, the invention relates to systems and methods for estimating phase measurements in MRI.

Numerous emerging MR applications are in need of accurate phase measurements. One of the main challenges with phase imaging is the ambiguity associated with such a regime. Phase offsets, noise, phase wrapping, and their interactions with each other introduce uncertainties and irregularities that so far have only been met with spatial regularization: assumptions about the smoothness of the underlying data. This inherently reduces the spatial resolution and accuracy of the measurements.

SUMMARY OF THE INVENTION

The present invention overcomes the aforementioned drawbacks by providing a system and method for estimating phase measurements while disambiguating the phase ambiguities in those measurements. Advantageously, the disambiguated phase measurements can then be used in various phase imaging applications, including estimating flow from the phase measurements; estimating physiological parameters and functions from the phase measurements; deriving functional information about neuronal activation from the phase measurements; and combining signals from multiple different receive channels.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for estimating phase measurements in MRI while resolving phase ambiguities in those measurements. As one aspect of this invention, systems and methods for combining measurements from multiple different receive channels in an MRI system while resolving phase ambiguities can be provided. For instance, one of the primary challenges with combining complex (magnitude and phase) measurements from multiple different receive channels is the underlying ambiguities in the phase measurements. As a particular example, the radio frequency ("RF") receive coils are out-of-phase, or offset, by a relative and unknown amount. This phase offset is also spatially varying. Other sources of phase ambiguities include phase wrapping (phase aliasing) and noise.

The systems and methods of the present invention are capable of overcoming these phase ambiguities using a joint acquisition and processing technique. The acquisition specifies two or more echo time steps at which the complex measurements are acquired. The corresponding reconstruction algorithm combines the complex data together in a way that disambiguates the phase. An optimizer that determines the values of the echo time steps, and the parameters of the post-processing algorithm, is provided. This optimizer only needs to be run once, offline, before acquisition.

Thus, using the systems and methods of the present invention, no phase unwrapping is needed, no denoising/smoothing is needed, no estimation of phase offsets is needed, and the results are free of the artifacts that are commonly seen in phase reconstruction methods. The technique can therefore yield very high resolution phase information.

With such a technique, the following important properties arise. First, a large dynamic range can be achieved without increasing the echo time sampling. Second, large echo time sampling can be used without being limited by phase-wrapping artifacts. Third, spatial regularization and phase unwrapping are not needed. The first two properties result in reduced phase uncertainty and increased robustness, while the third implies an increase in the resulting spatial resolution at a drastically reduced computation time.

The optimization technique implemented by the present invention uses a priori knowledge, or data, in combination with statistical analysis associated with the tissue, or sample, and is based on techniques described in co-pending Patent Application No. PCT US2013/022524, which is herein incorporated by reference in its entirety.

Before discussing the implementation of removing phase ambiguities when combining data from multiple receive channels, a discussion of the origin of the phase ambiguities in the signals acquired with a multichannel receiver is provided. It is noted that for single channel receiver systems, c=1 in the following mathematical description.

By way of example, the signal measurement, $g(x,y;c,TE_k)$ obtained using a gradient-recalled echo ("GRE") pulse sequence at a receiver channel element, c, can be written as, $$g(x,y;c,TE_k) = f(x,y;TE_k)e^{j(\phi_0^c(x,y)+2\pi\Delta B(x,y)TE_k)} + w(x,y) \quad (1);$$

where the magnitude term, $f^c(x,y;TE_k)$ is the spin density at echo time, $TE_k$, modulated by the sensitivity of the $c^{th}$ channel; $\Delta B(x,y)$ is the field offset value in Hertz at the location $(x,y)$; $\phi_0^c(x,y)$ is the spatially-varying phase offset for the $c^{th}$ channel; and $w(x,y)$ is a noise random variable. The noise, $w(x,y)$, is complex-valued and can be represented as Gaussian noise associated with a normal distribution, $N(0,\sigma_w)$, per the following:

$$w(x,y) = w_R(x,y) + iw_I(x,y) \text{ with } w_R, w_I \sim N(0, \sigma_w) \qquad (2).$$

Instead of measuring the actual phase, a numerically computed angle, $\psi_k^c(x,y)$, of the measurement, $g(x,y;c,TE_k)$, is computed as, $$\psi_k^c(x,y) = \phi_0^c(x,y) + 2\pi\Delta B(x,y)TE_k + \Omega_k^c(x,y) + 2\pi r_k^c(x,y) \qquad (3);$$

where $\Omega_k^c(x,y)$ is the radian phase contribution of the additive noise term, $w(x,y)$, and $r_k^c(x,y)$ is a phase wrapping integer that forces the sum of the first three terms on the right-hand side of Eqn. (3) to be in the range $[-\pi, \pi)$. Therefore, the integer $r_k^c(x,y)$ is a function of both echo time index, $k$, and channel index, $c$. Note that the noise contribution in the phase, $\Omega_k^c(x,y)$, depends on $f^c(x,y;TE_k)$ and thus is also a function of $TE_k$ and $c$.

Hereafter, the pixel subscripts, $(x,y)$, are dropped with the understanding that the remaining analysis applies separately to each voxel in the image. Also, the superscript $c$ is used to indicate a quantity that is channel-dependent while the subscript $k$ is used to indicate a quantity that is dependent on the echo time.

It is desired to reconstruct the phase term, $2\pi\cdot\Delta B\cdot TE_k$, from the angle measurements, $\psi_k^c$, of channels $c=1, 2, \ldots, M$, where M is total number of channels. At each voxel, there are four unknowns in Eqn. (3), however. These unknowns include the phase offset, $\phi_0^c$; the desired phase term, $2\pi\cdot\Delta B\cdot TE_k$; the phase-wrapping integer, $r_k^c$; and the noise contribution, $w$.

The four unknown parameters identified above are dependent on one another, thereby contributing to phase ambiguities. The noise contribution, $\Omega_k^c$, which is disregarded in much of the MRI phase imaging techniques, can be significant in some regions due to the sensitivity profile of the $c^{th}$ channel. Averaging the effect of noise variations across channels is not straightforward because the phase offsets, $\phi_0^c$, restrict the ability to perform a coherent addition of the channels' raw measurements. In other words, any linear operation on $g(c,TE_k)$ that does not compensate for each $\psi_k^c$ could suffer from loss of signal due to destructive interference. Thus, the angle, $\psi_k^c$, of a noisy phase is computed, which could yield a noise-induced phase-wrapping, even in regions of moderate SNRs. Moreover, the unknown phase-wrapping integer, $r_k^c$, can be affected by both phase-offsets, $\phi_0^c$, and phase signal accumulation, $2\pi\cdot\Delta B\cdot TE_k$. The ability of reconstructing the latter values is further subject to a fundamental tradeoff: small values are difficult to reconstruct even in moderate levels of SNR. For large values of phase, $2\pi\cdot\Delta B\cdot TE_k$, phase wrapping dominates.

The interdependency of these parameters makes the task at hand particularly challenging. Most common approaches address the each unknown parameter as follows.

Methods that resolve the phase offset ambiguity can be generally classified in one of two categories. In one, the phase offset is measured or estimated directly, and in the other, the phase offset parameter is mathematically eliminated.

Methods belonging to the former category generally includes measuring the phase offset for each channel. Phase conjugate methods are then used at each channel to remove the phase offsets. Next a sum of the "approximately coherent" raw data is taken over all the channels, in order to reduce the effect of noise. Finally, phase unwrapping is performed on the angle of the resulting data to address phase wrapping. The efficiency of these methods depends on the performance of the phase offset estimation step. The downsides of these methods include requiring a separate scan, registration, and phase unwrapping; assuming that the phase offset is constant; and suffering from artifacts due to noise/unwrapping singularities.

Methods belonging to the latter category include phase filtering and phase difference ("PD") methods. The downsides of these methods include reduced signal-to-noise ratio ("SNR"), phase wrapping and noise amplification, and a phase wrapping/SNR tradeoff. At large $B_0$ field strengths, such as 7 Tesla and above, PD methods also require phase unwrapping. PD is a more accurate methods for addressing the phase offset ambiguity, having the fewest artifacts and fastest computation time. The disadvantage of PD, however, is that it results in reduced contrast due to having to keep echo time step short.

Noise has been ignored for the most part in many methods. The only merit it has been given is a smoothing filter which eventually reduces the resolution of the image.

Phase-unwrapping methods attempt to determine, at each spatial location, what variations are purely due to noise, phase jumps from signal accumulation, or noise-induced phase wrapping. Even with knowledge of the phase offset, $\phi_0^c$, the phase unwrapping problem is NP-hard in two-dimensions and higher. Some methods use plenty of echoes, which inhibits acquisition times, and others use a single echo. Implications of phase unwrapping methods include reduced resolution, additional processing, user intervention, and artifacts at high resolution. Phase unwrapping methods also limit the desired minimum echo time spacing in rapid multi-echo pulse sequences.

In contrast to previous methods, the systems and methods of the present invention address phase ambiguities by determining optimal echo time spacings that result in distinct phase information that can be used to resolve the phase ambiguities.

To deal with the unknown phase offset, $\phi_0^c$, a phase conjugation step of signals associated with two echoes, $TE_0$ and $TE_1$, is first applied. Second, a coherent sum over all the channels is performed according to, $$g_{0,1} = \sum_c g_0^c (g_1^c)^* . \qquad (4)$$

The resulting phase slope estimate, $\widetilde{\Delta B_{0,1}}$, computed from the angle of $g_{0,1}$ can be written as, $$\widetilde{\Delta B_{0,1}} = \Delta B + \frac{n_{0,1} + \frac{\Delta\Omega_{0,1}}{2\pi}}{\Delta TE_{0,1}} ; \qquad (5)$$

where $\Delta\Omega_{0,1} = \Omega_1 - \Omega_0$ is the difference between the phase noise random variables in Eqn. (3), and $n_{0,1}$ denotes a phase wrapping integer that is non-zero whenever $2\pi\cdot\Delta B\cdot\Delta TE_{0,1} + \Delta\Omega_{0,1}$ falls outside of the interval $[-\pi, \pi)$. A similar phase slope estimate can be computed for the echo pair occurring at echo times $TE_0$ and $TE_2$, $$\widetilde{\Delta B_{0,2}} = \Delta B + \frac{n_{0,2} + \frac{\Delta \Omega_{0,2}}{2\pi}}{\Delta TE_{0,2}};\quad(6)$$

These estimates still suffers from noise and phase-wrapping ambiguities. To resolve this, an adaptation of the maximum ambiguity distance for phase imaging ("MAGPI") method described in Patent Application No. PCT US2013/022524 is utilized. The choice of echo step, ΔTE, defines three reconstruction performance regimes with respect to a cutoff given by, $$\Delta B_{cutoff} = \frac{1}{2\Delta TE}.\quad(7)$$

The contribution of each of phase wrapping and noise to the overall reconstruction error is determined by the value of ΔB with respect to $\Delta B_{cutoff}$. Whenever ΔB in a given voxel is larger than $\Delta B_{cutoff}$, phase wrapping (aliasing) dominates the error in that voxel. To avoid such a wrapping-limited regime (Regime I, hereafter), a small value of ΔTE is favored. On the other hand, in voxels where ΔB is small, noise dominates the error in Eqn. (3) (Regime II) and a large value of ΔTE should be sought. Most PD methods choose moderate values for ΔTE (Regime III) in an attempt to trade-off Regimes I and II. However, in addition to noise and phase-wrapping, Regime III is also amenable to noise-driven phase wrapping errors. This ambiguity requires the use of complex processing methods to decouple slope errors from their phase wrapping and noise contributions. Common methods use a combination of spatial regularization and phase unwrapping algorithms to constrain these inherent errors.

Figure 1A:
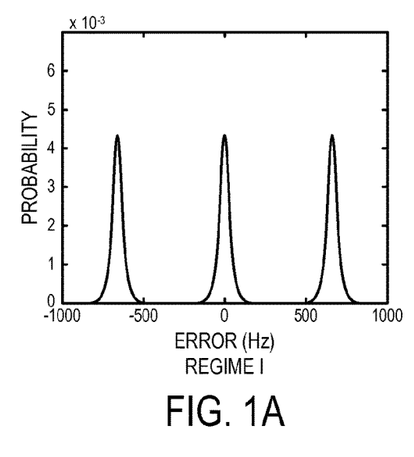
FIGS. 1A-1D are graphs of phase ambiguity functions at echo times chosen using Regime I, Regime II, Regime III, and MAGPI techniques, respectively.
Figure 1B:
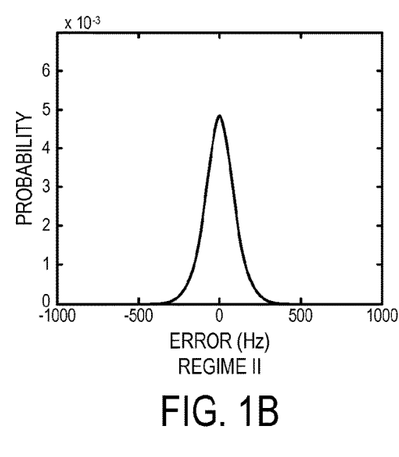
Figure 1C:
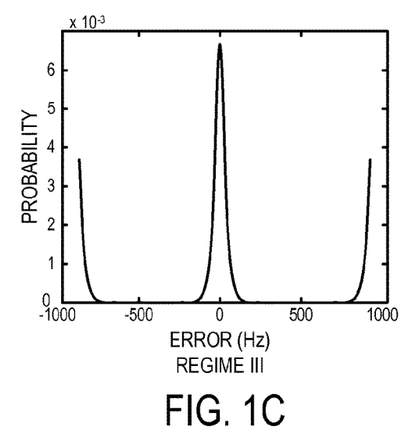

The ambiguity in the original phase for a given echo step and a given receive channel can be derived in closed-form. This phase-ambiguity ("PA") function embodies the trade-offs for a given ΔTE. Example PA functions are shown in FIGS. 1A-1C, corresponding to scenarios in each of the regimes. The ideal PA function is one that is a delta function (i.e., an impulse response) at zero, resulting in the situation where only the original true phase value is the solution to Eqn. (5) above. Naturally, this is not physically possible to achieve.

Figure 1D:
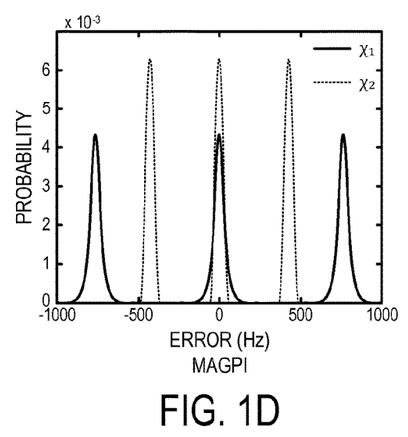

Instead, the inherent phase ambiguities can be resolved using an optimal choice of two echo steps, $\Delta TE_{0,1}$ and $\Delta TE_{0,2}$, and its resulting channel-dependent PA functions $\chi_1$ and $\chi_2$. The simple echo optimizer essentially engineers the PA functions from each echo pair, $\chi_1$ and $\chi_2$, to possess specific distinct features. Then, by using a simple estimation routine, the original phase value could be recovered from the joint pattern of PA functions. An example optimal PA function pair is shown in FIG. 1D, where $\chi_1$ and $\chi_2$ are engineered to have a maximum $L_2$ distance between the incorrect (noisy and/or wrapped) solutions. Note that both PA functions live in regime I, which is heavily limited by phase wrapping; however, the unique pattern of the PA functions could be used in a simple estimation routine to recover the original phase slope.

The search for such "optimal" echo spacings is performed using a numerical routine that takes into account the imaging scenarios. The imaging scenarios that affect the resulting echo spacings include the minimum expected SNR in a voxel, the minimum expected $T_2^*$ in a voxel, the minimum attainable echo time spacing with the pulse sequence of choice, and the maximum expected dynamic range in the phase slope (in Hz). Because the optimizer can be run offline once, these imaging scenarios could be tabulated as a function of the resulting optimal echo time spacing.

Mathematically, the proposed echo time optimization routine solves the following problem:

$$[TE_0^{opt}, TE_1^{opt}, TE_2^{opt}] = \underset{[TE_0^{opt}, TE_1^{opt}, TE_2^{opt}]}{\operatorname{argmax}} \mathcal{D}(\chi_1, \chi_2);\quad(8)$$

such that $[TE_0^{opt}, TE_1^{opt}, TE_2^{opt}] \in T$; and where $D(\chi_1, \chi_2)$ denotes the distance between $\chi_1$ and $\chi_2$, and where T is the set of allowable echo times that could be utilized with the pulse sequence of choice. Note that once ΔB is recovered, the phase could be synthesized at any of the three echo contrasts. Also, one of the echo times could be constrained to be equal to a specific value of interest.

Various distance measures, $D(\chi_1, \chi_2)$, can be considered in order to maximize the distinction between $\chi_1$ and $\chi_2$. As an example, a geometric measure based on maximizing the minimum distance between respective peaks from $\chi_1$ and $\chi_2$ can be used; however, this measure alone would attempt to decrease the echo time spacings, which reduces the peaks' spacing but also broaden the peaks. The latter is undesirable because minimizing the overlap between the center peak of $\chi_1$ and that of $\chi_2$ is also desired, corresponding to the noisy wrap-free solution. By way of example, the overall objective function, $D(\chi_1, \chi_2)$, can thus combine these two geometrical metrics, namely, $D(\chi_1, \chi_2)$ can equal the difference between the minimum distance between $\chi_1$ and $\chi_2$ peaks and the total width of the central peaks.

The only prior information needed to compute the optimal echo times with MAGPI are the maximum dynamic range of interest, $2\delta B_{max}$; the minimum signal-to-noise ratio, $SNR_0$; and the minimum expected $T_2^*$ in the regions of interest. The optimization problem can be solved using an adaptive simulated annealing ("ASA") routine. The echoes optimized by Eqn. (8) allow the resulting PA functions to be maximally distinct, in the sense defined by the metric $D(\chi_1, \chi_2)$ above. The optimization routine of Eqn. (8) can be run offline, once.

A corresponding estimation method can be provided that takes advantage of the designed ambiguity space in order to estimate disambiguated phase measurements. Similar to the distance metric, $(\chi_1, \chi_2)$, this estimation algorithm is based on an intuitive geometrical approach.

Because the two PA functions are optimized to be maximally distant, the two values from these PA functions that are closest to one another (e.g., in the $L_2$-distance sense) correspond to the two phase wrap-free peaks from $\chi_1$ and $\chi_2$. A phase measurement estimate can be recovered by, for example, averaging these two closest values.

This closest $L_2$-distance ("CL2D") estimation method includes computing angle locations for each pair of echoes. That is, for each echo pair, (0, 1), the angle location (x,y) is computed. The result yields $\widetilde{\Delta B_{0,1}}$ (x,y) in Eqn. (5), which constitutes one realization from the PA function, $\chi_1$. The procedure is repeated for the next echo pair, (0, 2), to obtain a value for $\widetilde{\Delta B_{0,2}}$ (x,y). The phase slope values, $\widetilde{\Delta B_{0,1}}$ (x,y) and $\widetilde{\Delta B_{0,2}}$ (x,y), are then replicated by the respective optimized echo spacings, $1/\Delta TE_{0,1}$ and $1/\Delta TE_{0,2}$, over the dynamic range of interest Together, these values constitute sets of values from each PA function, $\chi_1$ and $\chi_2$, that would solve Eqns. (5) and (6), respectively.

The solutions that produce peaks centered around the original phase values are identified. As described above, the present invention recognizes that such solutions are closest, in the $L_2$ sense, to one another. This recognition utilizes the prior information that all the peaks are designed by the optimizer to be maximally distant.

The phase measurements are estimated as the weighted average of these closest two samples. The weighting can be designed to take into account the respective echo times. For example, later echoes may have a lower weighting to account for $T_2^*$ effects. Note that instead of a simple averaging, other estimation methods can be used. It is also noted that the CL2D estimation method can be applied independently, one voxel at a time.

The systems and methods of the present invention preferably utilize data acquired from three echoes. By way of example, this data can be acquired using a multi-echo gradient-recalled echo ("GRE") sequence. Note that the echo time spacing is constrained by the multi-echo GRE sequence. This constraint can be incorporated into the optimization problem. Even though three echoes can be acquired using three separate GRE pulse sequences, without any constraint on the echo spacing, that strategy takes longer and introduces the risk for subject motion in between scans.

Phase reconstruction performs the following steps, First, the phase offset, $\phi_0^c$, is cancelled as discussed above. Then, a sum of all the channels for the echo pairs ($TE_0$, $TE_1$) and ($TE_0$, $TE_2$) is computed. The CL2D reconstruction algorithm described above and in co-pending Patent Application No. PCT US2013/022524 is then applied, one voxel at a time. It is also noted that other estimation methods could be implemented at the final step.

Figure 2:
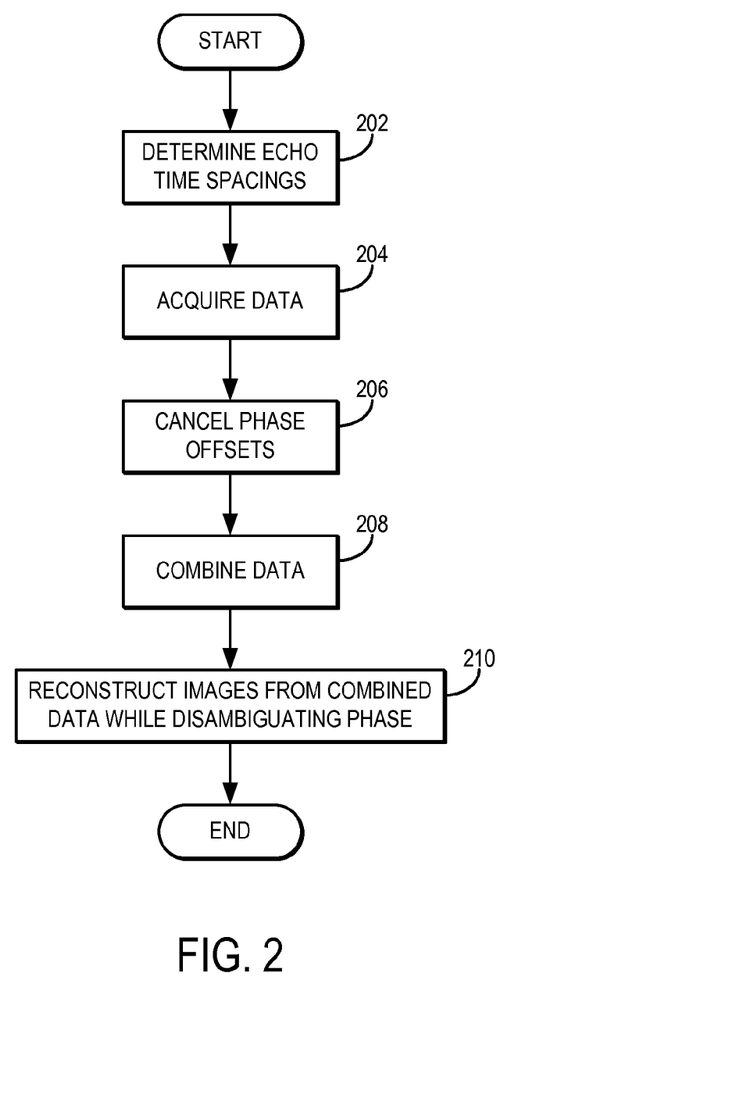
FIG. 2 is a flowchart setting forth the steps of an example of a method for estimating phase measurements in multiple different receiver channels and combining the resulting phase measurements.

Referring now to FIG. 2, a flowchart setting forth the steps of an example of a method for combining measurements from multiple different receive channels and reconstructing an image from the combined data is illustrated. First, the optimal echo times are selected, as indicated at step 202. For instance, two or more echo time spacings are determined. Each echo time spacing defines the duration of time between a pair of echoes, thus, three or more echoes occurring at echo times determined by the echo time spacings will be acquired. Using the determined echo time spacings, a pulse sequence is performed to acquire data at multiple different echo times, as indicated at step 204. The phase offset, $\phi_0^c$, for each receive channel is then canceled from the acquired data, as indicated at step 206. This process is performed as described above. The data is then combined by computing a sum of all of the channels for the echo pairs, as indicated at step 208. For instance, the sum of all the channels for echo pairs ($TE_0$, $TE_1$) and ($TE_0$, $TE_2$) is computed. A modified MAGPI reconstruction is then performed, as indicated at step 210, to reconstruct an image in which phase ambiguities and the associated artifacts have been substantially mitigated.

Although the preceding example describes a method for estimating phase measurements that are substantially free of phase ambiguities for the use combining measurements from multiple different receiver channels, it will be appreciated by those skilled in the art that the generalized phase estimation framework described here can be applied to many different imaging applications. For example, a more robust phase measurement estimated using the techniques of the present invention can be utilized for different phase imaging applications, including estimating flow; estimating physiological parameters and functions based on phase measurements; and assessing functional neuronal activation. Examples of physiological parameters and functions that are based on phase measurements, and thus can be estimated using the present invention, include oxygenated/deoxygenated blood, paramagnetic iron heme, iron deposits, blood flow, paramagnetic nanoparticles, and chemical content such as water or fat fraction.

Figure 3:
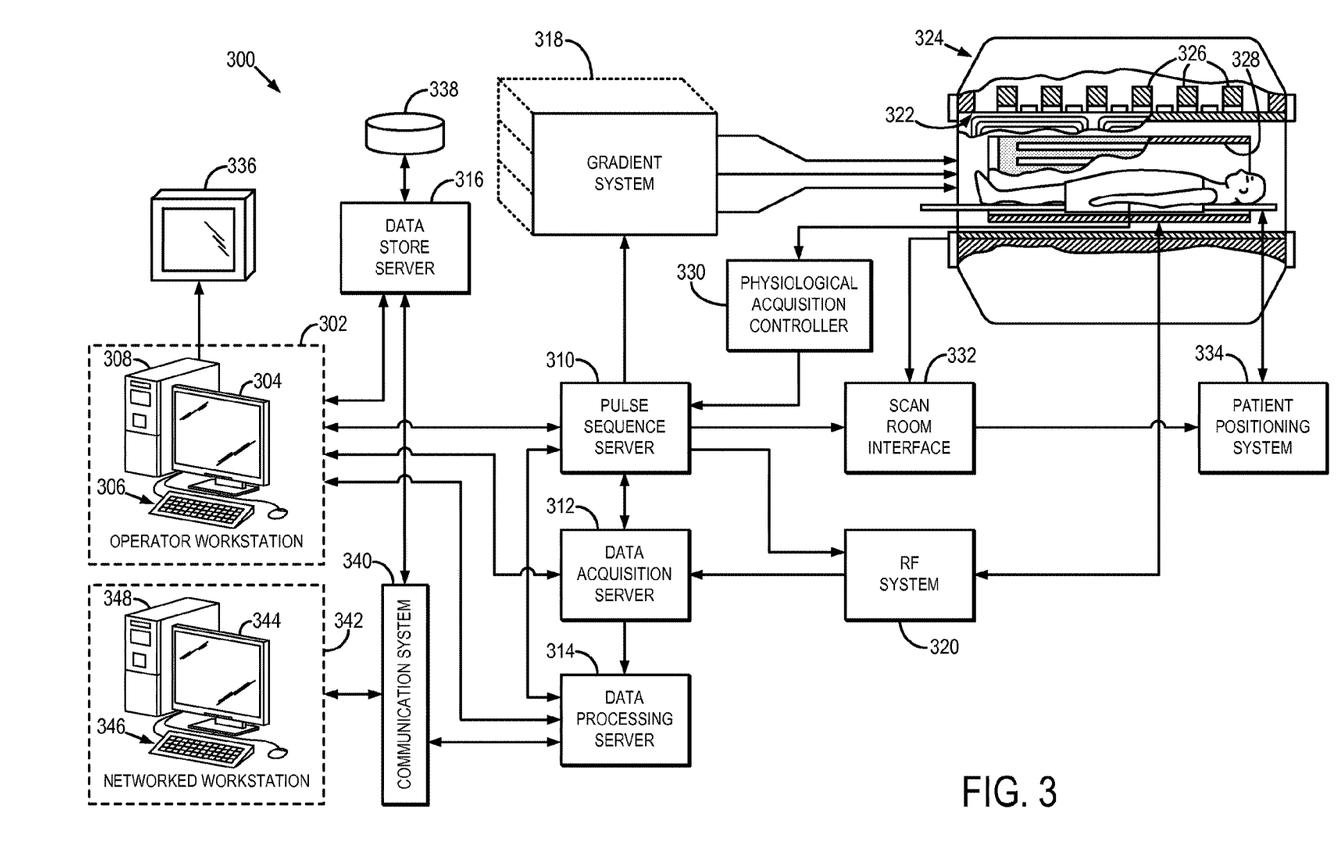
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes a workstation 302 having a display 304 and a keyboard 306. The workstation 302 includes a processor 308, such as a commercially available programmable machine running a commercially available operating system. The workstation 302 provides the operator interface that enables scan prescriptions to be entered into the MRI system 300. The workstation 302 is coupled to four servers: a pulse sequence server 310; a data acquisition server 312; a data processing server 314; and a data store server 316. The workstation 302 and each server 310, 312, 314, and 316 are connected to communicate with each other.

The pulse sequence server 310 functions in response to instructions downloaded from the workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding MR signals. The gradient coil assembly 322 forms part of a magnet assembly 324 that includes a polarizing magnet 326 and a whole-body RF coil 328.

RF excitation waveforms are applied to the RF coil 328, or a separate local coil (not shown in FIG. 3), by the RF system 320 to perform the prescribed magnetic resonance pulse sequence. Responsive MR signals detected by the RF coil 328, or a separate local coil (not shown in FIG. 3), are received by the RF system 320, amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the scan prescription and direction from the pulse sequence server 310 to produce RF pulses of the desired frequency, phase, and pulse amplitude waveform. The generated RF pulses may be applied to the whole body RF coil 328 or to one or more local coils or coil arrays (not shown in FIG. 3).

The RF system 320 also includes one or more RF receiver channels. Each RF receiver channel includes an RF preamplifier that amplifies the MR signal received by the coil 328 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (9);$$

and the phase of the received MR signal may also be determined:

$$\varphi = \tan^{-1}\left(\frac{Q}{I}\right). \qquad (10)$$

The pulse sequence server 310 also optionally receives patient data from a physiological acquisition controller 330. The controller 330 receives signals from a number of different sensors connected to the patient, such as electrocardiograph ("ECG") signals from electrodes, or respiratory signals from a bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized MR signal samples produced by the RF system 320 are received by the data acquisition server 312. The data acquisition server 312 operates in response to instructions downloaded from the workstation 302 to receive the real-time MR data and provide buffer storage, such that no data is lost by data overrun. In some scans, the data acquisition server 312 does little more than pass the acquired MR data to the data processor server 314. However, in scans that require information derived from acquired MR data to control the further performance of the scan, the data acquisition server 312 is programmed to produce such information and convey it to the pulse sequence server 310. For example, during prescans, MR data is acquired and used to calibrate the pulse sequence performed by the pulse sequence server 310. Also, navigator signals may be acquired during a scan and used to adjust the operating parameters of the RF system 320 or the gradient system 318, or to control the view order in which k-space is sampled. In all these examples, the data acquisition server 312 acquires MR data and processes it in real-time to produce information that is used to control the scan.

The data processing server 314 receives MR data from the data acquisition server 312 and processes it in accordance with instructions downloaded from the workstation 302. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 314 are conveyed back to the workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the workstation 302. The workstation 302 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

What is claimed is:

1. A method for estimating a phase of a magnetic resonance signal using a magnetic resonance imaging (MRI) system, the steps of the method comprising:

a) determining with a computer system at least two echo time spacings that define a duration of time between pairs of echo times, the at least two echo time spacings being determined by optimizing phase ambiguity functions that are associated with the at least two echo time spacings;

b) acquiring data by directing a radio frequency (RF) system and a gradient system of the MRI system to perform a pulse sequence that includes forming echoes at a plurality of echo times that are spaced apart in time using the determined at least two echo time spacings; and c) estimating with a data processing server of the MRI system a phase value at each voxel location in an image matrix using the acquired data and the determined at least two echo time spacings.

2. The method as recited in claim 1 in which the data acquired in step b) is acquired from a subject in which a fluid is flowing, and in which the method further comprises determining with the data processing server a flow value associated with the fluid at voxel locations in the image matrix using the phase values estimated in step c).

3. The method as recited in claim 2 in which the fluid is at least one of blood, cerebrospinal fluid, and air.

4. The method as recited in claim 1 in which the data acquired in step b) is acquired from a subject, and in which the method further comprises computing with the data processing server at least one of a physiological parameter of the subject and a measure of a physiological function of the subject using the phase values estimated in step c).

5. The method as recited in claim 4 in which the measure of the physiological function is a measure associated with neuronal activity.

6. The method as recited in claim 1 in which step a) includes optimizing the phase ambiguity functions with the computer system by maximizing a distinctiveness of each phase ambiguity function with the computer system.

7. The method as recited in claim 6 in which the distinctiveness of each phase ambiguity function is maximized by maximizing distances between the phase ambiguity functions with respect to a defined distance metric.

8. The method as recited in claim 7 in which the defined distance metric includes an $L_2$ distance.

9. The method as recited in claim 1 in which step a) includes determining with the computer system the at least two echo spacings using a numerical routine that takes into account at least one of a minimum expected signal-to-noise ratio (SNR), a minimum expected transverse relaxation time, a minimum attainable echo time spacing for a given pulse sequence, and a maximum expected dynamic range in a phase slope.

10. A method for resolving phase ambiguities in magnetic resonance signals acquired using a magnetic resonance imaging (MRI) system and a multichannel receiver, the steps of the method comprising:

a) determining with a computer system at least two echo time spacings that define a duration of time between pairs of echo times, the at least two echo time spacings being determined by optimizing phase ambiguity functions of receiver elements in the multichannel receiver that are associated with the at least two echo time spacings;

b) acquiring data on each of a plurality of channels of the multichannel receiver by directing a radio frequency (RF) system and a gradient system of the MRI system to perform a pulse sequence that includes forming echoes at a plurality of echo times that are spaced apart in time using the determined at least two echo time spacings;

c) combining with a data processing server of the MRI system the data associated with each of the plurality of channels of the multichannel receiver; and d) reconstructing with the data processing server an image from the combined data.

11. The method as recited in claim 10 in which step a) includes optimizing the phase ambiguity functions with the computer system by maximizing a distinctiveness of each phase ambiguity function with the computer system.

12. The method as recited in claim 11 in which the distinctiveness of each phase ambiguity function is maximized by maximizing distances between the phase ambiguity functions with respect to a defined distance metric.

13. The method as recited in claim 12 in which the defined distance metric includes an $L_2$ distance.

14. The method as recited in claim 10 in which step a) includes determining with the data processing server the at least two echo spacings using a numerical routine that takes into account at least one of a minimum expected signal-to-noise ratio (SNR), a minimum expected transverse relaxation time, a minimum attainable echo time spacing for a given pulse sequence, and a maximum expected dynamic range in a phase slope.

* * * * *